ions related to the rotational speed of the tool. If so, a "failure" signal is produced which may be used, for example, to cause retraction of the tool.

United States Patent [19]
Yee et al.

[11] Patent Number: 4,471,444
[45] Date of Patent: Sep. 11, 1984

[54] ROTATING TOOL WEAR MONITORING APPARATUS

[75] Inventors: Kenneth W. Yee, Rockville, Md.; Donald S. Blomquist, Vienna, Va.

[73] Assignee: The United States of America as represented by the Secretary of Commerce, Washington, D.C.

[21] Appl. No.: 364,944

[22] Filed: Apr. 2, 1982

[51] Int. Cl.³ .............................................. G06F 15/46
[52] U.S. Cl. .................................. 364/475; 364/508; 364/551; 73/104
[58] Field of Search ............... 364/475, 507, 508, 550, 364/551, 566; 73/104, 558–660; 408/8–13; 340/683

[56] References Cited

U.S. PATENT DOCUMENTS

| | | | |
|---|---|---|---|
| 3,819,916 | 6/1974 | Watanabe | 364/475 X |
| 3,834,615 | 9/1974 | Watanabe et al. | 364/475 X |
| 3,841,149 | 10/1974 | Edwin et al. | 364/508 X |
| 3,872,285 | 3/1975 | Shum et al. | 73/104 X |
| 4,176,395 | 11/1979 | Howatt | 364/551 |
| 4,228,514 | 10/1980 | Weiss | 364/475 X |
| 4,326,257 | 4/1982 | Sata et al. | 364/508 |

*Primary Examiner*—Jerry Smith
*Assistant Examiner*—Allen MacDonald
*Attorney, Agent, or Firm*—Eugene J. Pawlikowski; Alvin J. Englert

[57] ABSTRACT

A system is provided for predicting when the failure of a rotating machine tool or part is imminent or when a tool is worn. The system includes a transducer for producing an output related to the workpiece vibrations caused by the machine tool and an analog comparator which compares this output with a threshold signal related to the normal operation of the tool and established by a microcomputer which determines whether further signals which exceed the threshold are produced during each of a predetermined number of subsequent time intervals related to the rotational speed of the tool. If so, a "failure" signal is produced which may be used, for example, to cause retraction of the tool.

10 Claims, 3 Drawing Figures

ROTATING TOOL WEAR MONITORING APPARATUS

FIELD OF THE INVENTION

The present invention is directed to apparatus for monitoring the wear on a rotating machine tool or part so as to determine when failure of the tool or part is imminent.

BACKGROUND OF THE INVENTION

Drilling is an example of a manufacturing operation that requires tooling which inherently wears out or fails as the operation proceeds. When a small drill is used on a large machining center, a worn drill will always fail if the use thereof is continued beyond a particular wear limit. If the wear process occurred at a predictable rate a drill could be replaced at the optimum time in accordance with this rate. However, the wear process is not predictable with any degree of certainty and depends upon such variables as cutting edge sharpness, symmetry of the cutting edge, local change in material hardness, and lubrication. Thus, one drill may drill more than 2,000 holes during the lifetime thereof, while another may drill less than 100 holes before failure.

It is evident that a number of benefits would result from the ability to measure the wear of a cutting tool during the cutting process. For example, productivity would increase because optimum tool replacement times could be determined. Further, the ability to be able to determine that a tool has failed is useful since with this information the machining center can be prevented from attempting to feed the remains of a machine tool into the work. It will be appreciated that it is much easier to remove a broken drill if part of the drill remains above the surface of the workpiece. In this regard, "peck" drilling, the drill may be broken off flush with the workpiece surface or driven into the hole on the second peck after the drill has broken. Alternatively, the broken drill may slide off the piece of drill embedded in the workpiece and severely damage the surface.

Prior art systems that measure the power consumption of the machining center as an indication of tool wear are described in Beer, Larry D., "Power Consumption - A Measure of Tool Performance", Technical Paper MR79-398, Am. Soc. of Mechanical Engineers. Such systems can, however, only be used when a measurable amount of power is consumed in the machining operation in excess of that used for turning the spindle motor. Other methods such as measuring the cutting forces or temperature have generally been unsuccessful when a small tool is used in a large machining center.

Other prior art systems use signature analysis of the vibration from the machining operation as an indication of tool wear. Some systems of this type are described in Micheletti, G. F., Rossetto, S., and Ponti, M., "Tool Vibration Pattern and Tool Life on Automatic Screw Machine", Advances in M.T.D.R., Vol. A. Sept. 1970, 145-159; Young, F. W., "An Investigation of Available Signals for Adaptive Control Machine Tools", S.M. Thesis, Mechanical Engineering Dept., Mass. Inst. of Tech. May 1970; and Gaudreau, M., "An On-Line Technique for Tool Wear Measurement", M.S. Thesis, Dept. of Aeronautic and Astronautics, Mass. Inst. of Tech., June 1975. These systems have been of limited success. Other systems use spectral analysis to determine the amount of tool wear and this approach has disadvantages with respect to constant complexity. Such systems are described in Edwin, A., and Vlach, T., "A New Approach to Tool Wear Monitoring", Proceedings of the 27th Annual Conference and Exhibition of the Instrumentation Society of America, Oct. 1972; Weller, E. J., and Welchbrodt, B., "Listen to Your Tools-They're Talking to You", Technical Paper No. MR67444, Soc. of Mfg. Engineers; Weller, E. J. Schrier, H.M., and Welchbrodt, B., "What Sound Can be Expected from a Worn Tool?", A.S.M.E., J. Eng. for Industry, Aug. 1969, pp. 525-534; Lutz, J., Societe National des Petroles D'Aquitaire, Paris, France; and U.S. Pat. No. 3,714,822, entitled "Process Measuring Wear on a Drilling Tool".

Prior art patents of interest include U.S. Pat. Nos. 3,745,815 (Bentone et al.) and 3,979,739 (Bircchall). The Bentone et al patent discloses a device for evaluating the vibrations of a revolving member such as a bearing which device includes a detecting head incorporating an accelerometer, a detecting and amplifying circuit for amplifying and filtering signals generated by the detecting head in response to the vibrations referred to, a first amplitude discriminating circuit, a monostable multivibrator, an integrating circuit, a further amplitude discriminating circuit and relay. The monostable multivibrator produces pulses responsive to signals of an amplitude in excess of a threshold value set by the first discriminator circuit and the relay is activated only when a predetermined number of pulses (10 in a specific embodiment is received by the integrator. When this number of pulses is received, the resultant integrated output voltage is in excess of the threshold level set by the second amplitude discriminator and the relay is energized to, for example, automatically reject the bearing under test.

The Birchall patent discloses an apparatus for the detection of vibrations in rotating machinery wherein a transducer generates a signal whose amplitude corresponds to the amplitude of the machine under test and a comparator produces distinct outputs, i.e., a logic "1" or "0", depending on whether the transducer signal lies outside an acceptable range. If an "unacceptable" output is produced, the time during which this output persists is measured and the system is reset if the output does not persist for a predetermined time period. If the output does persist for that period, an alarm is actuated.

Summary of The Invention

In accordance with the invention, an apparatus or system is provided for monitoring the operation of a rotating tool or part and for producing an output indicative that the tool is about to fail, i.e., the system "measures" tool wear and predicts tool failure, and thus provides the advantages discussed above. In addition, the system of the invention overcomes the disadvantages associated with prior art systems which attempt to perform the same or a similar function. For example, in contrast to systems using spectral analysis, the system of the invention employs time-domain analysis to determine tool wear, thereby greatly reducing the complexity and cost as compared with spectral analysis systems and reducing analysis time to allow prediction. In this regard, a single chip microcomputer can be employed to carry out the basic operations. Further, in comparison with systems such as disclosed in the Bentone et al and Birchall patents discussed above, the system of the invention distinguishes over these prior art systems in at least two important respects. Specifically, the system: (1) uses adaptive techniques to determine a reference level for triggering an output signal, based on a signal reflective of normal operation, and (2) employs synchronous detection related to the period of rotation. It is important to note that neither the Bentone patent nor the Birchall patent provides for use of a detection mechanism which is synchronous with the metal removal process. The system of the invention uses this approach for tool failure or wear-rate detection and this greatly reduces the changes for a false alarm. For example, in many machining operations, it is common for a machinist to use a metal strip to remove chip buildup. This operation can produce a vibration signal that could result in the 10 pulses required by the system of the Bentone et al patent or pulses that occur for the amount of time required by the system of the Birchall patent. However, these pulses would not be synchronous with the machining operation and would not trigger the system of the present invention. There are, of course, other examples where the two other systems would be triggered when tool failure was not imminent or tool wear had not occurred.

It is noted that not only does the time-domain analysis provided in accordance with the invention reduce the number of parts as compared to spectral analysis, time-domain analysis also reduces the time required for the analysis, i.e., the time required to predict tool failure. The reason for this is that spectral analysis increases the number of degrees of freedom in the system and thus increases the uncertainty of the measurement. For example, a 512-point Fast Fourier Transform increases the uncertainty by thesquare root of 512. Therefore, instead of making the decision that a drill was about to fail in four revolutions, at least 22 revolutions would be required. These long times could result in catastrophic consequences-a broken tool.

Recognition of the deterministic nature of tool wear underlies the present invention and has resulted in a system that enables tool failure to be predicted with a precision that is not possible with prior art systems. That this is so will become evident from the discussion of the operation of the invention found hereinbelow.

According to a preferred embodiment of the invention, a system is provided for monitoring the operation of a rotating machine tool or part and for producing an output indicating that failure of that rotating tool or part is imminent, or that excessive wear of that tool or part is present, the system comprising: transducer means for producing an electrical output signal responsive to the mechanical vibrations produced by the tool or part being monitored; comparator means for comparing the output signal produced by the transducer means with a variable threshold signal related to normal operation of the tool or part being monitored and for producing an output when the output signal of the transducer means exceeds that threshold signal; and monitoring and calibrating means for, (1) during a monitoring mode of operation of the system, monitoring the comparator means to detect when an aforesaid output is produced by the comparator means, and producing a control signal indicating that failure of the tool or part is imminent or that excessive wear of the tool or part is present when, upon initially detecting such an output from the comparator, a further such output is also detected during each of a predetermined number of successive time intervals whose duration is related to the rotational speed of the tool or part; and for, (2) during a calibration mode of operation of the system, monitoring the output produced by the transducer means during the normal operation of the tool or part to establish the variable threshold signal referred to above.

In specific embodiment, the monitoring and calibrating means comprises a microcomputer and while this embodiment is preferred, it is also contemplated, as explained elsewhere, that random logic could also be used. In this specific embodiment, a means, advantageously a monostable multivibrator, is connected to the comparator means for producing an output pulse when the output signal of the transducer means exceeds the threshold signal and, in this embodiment, the monitoring and calibrating means monitors the output pulses produced by this output pulse producing means. As is also explained elsewhere, in an alternate, preferred embodiment, the use of monostable multivibrators is replaced with software. The pulse producing means (monostable multivibrator) preferably produces a pulse whose duration is slightly less than the period of rotation divided by the number of cutting edges or segments of the tool or part and the monitoring and calibrating means (microcomputer), upon initially detecting such a pulse, samples the output of the pulse producing means at time intervals equal to the period of rotation of said tool or part. Advantageously, the microcomputer, during the calibration mode of operation, reduces the threshold level from a predetermined fraction of the full scale voltage value by predetermined increments for predetermined intervals until a level is reached wherein a selected number of such pulses are sampled by the microcomputer, the microcomputer then generating, as the threshold signal, a signal which is a predetermined multiple of the level reached.

The transducer means preferably comprises an accelerometer and, advantageously, a piezoelectric accelerometer mechanically coupled to a workpiece associated with the tool or part. An amplifier having a high input impedance is preferably connected to the output of the accelerometer.

Other features and advantages of the invention will be set forth in, or apparent from, the detailed description of a preferred embodiment which follows.

Description of the Preferred Embodiments

Figure 1:
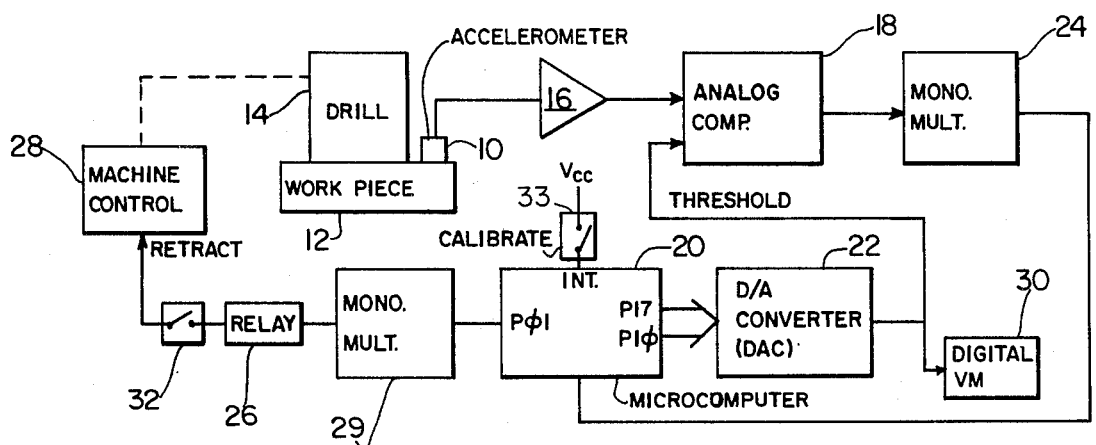
FIG. 1 is a schematic diagram, in block form, of the system of the invention.

Referring to FIG. 1, a schematic diagram of the overall system of the invention is shown. The system includes a transducer in the form of an accelerometer 10, mounted on a workpiece, indicated at 12, so as to respond to vibrations produced by the cutting operation of a rotating machine tool, indicated by block 14. It will be understood that, while the invention is described in connection with determining drill failure or drill wear, the invention is not limited to such use and could, for example, be used in determining wear in end mills, boring bars, shell mills, and other tools.

The output of the accelerometer 10 is connected to a highimpedance amplifier 16. The amplified accelerometer signal produced by the amplifier 16 is applied to one input of an analog comparator 18. The other input of the comparator 18 is connected to receive a threshold signal. This latter signal is derived from the accelerometer signal by a microcomputer 20 based on an automatic calibration routine described hereinbelow. A digital-to-analog converter (DAC) 22 is connected to the output of the microcomputer 20 and serves to convert the microcomputer output signal into an analog threshold input signal for the comparator 18.

The output of the analog comparator 18 is connected to a monostable mulivibrator (one-shot) 24. Voltage peaks in the signal which exceed a predetermined threshold provide triggering of the monostable multivibrator 24 which, in turn, produces a corresponding pulse having a width slightly less than the reciprocal of the product of the number of cutting edges of the machine tool and the tool rotational speed. In a specific example, a pulse width of 5.5 ms is provided for a two-fluted drill at a rotational speed of 4800 rpm. This approach provides two pulses per revolution in circumstances where the machine tool has two cutting flutes and both edges of the drill bit hit the workpiece.

The output of the monostable multivibrator 24 is applied to the microcomputer 20 which determines when a pulse is detected. When a pulse is detected, the microcomputer delays for approximately one half the reciprocal of the product of the number of cutting edges of the machine tool and the tool rotational speed and then samples the signal at the same input at time intervals equal to the period of the tool rotation to thereby provide synchronous detection. It is advantageous to provide the delay in order to allow for small variations in the machine-tool rotational speed due to cutting loads. In the specific embodiment referred to, these intervals are approximately 12.5 ms for a rotational speed of 4800 rpm. If pulses are detected (i.e., pulses produced by the monostable multivibrator 24 and caused by successive accelerometer signals greater than the threshold), the input is sampled at rotation period intervals until a predetermined number (e.g., four in a specific embodiment) of pulses in sequence is detected. It is important to note that if, for any sample, a pulse is not detected, the microcomputer resets and looks for a "new" first pulse.

Figure 2:
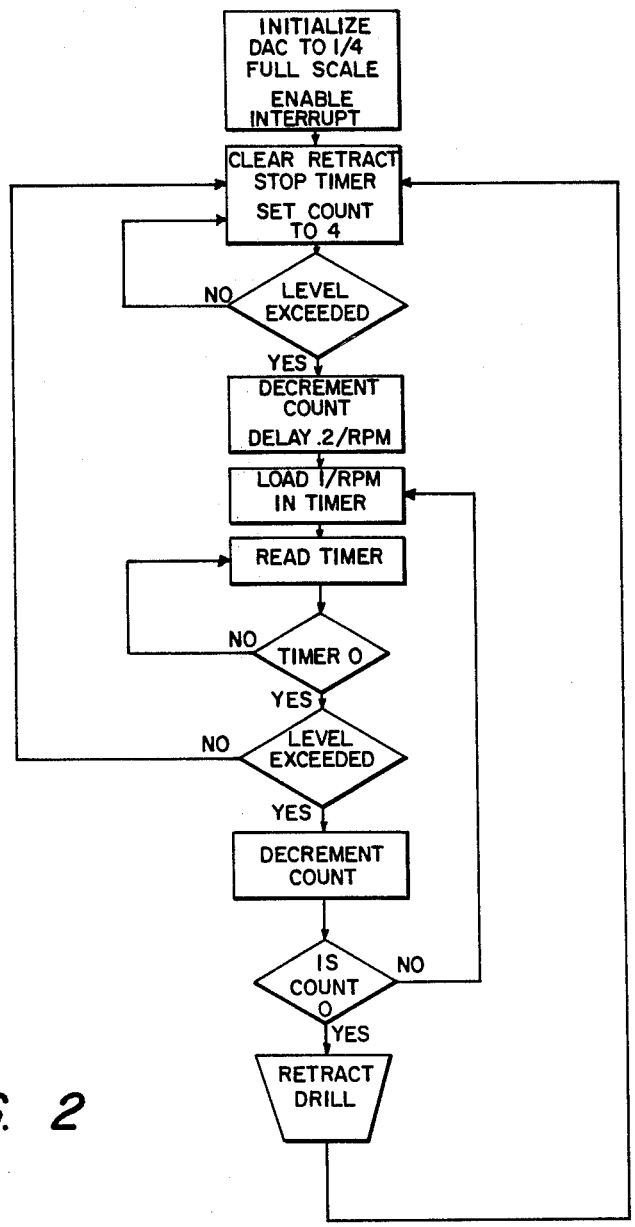
FIG. 2 is a flow chart or diagram of the drill detection operation.

When a fault condition exists, i.e., when four pulses in a row are detected, the microcomputer 20 produces an output signal which, for the specific embodiment, causes the opening of a normally closed relay 26 connected in series with the emergency "Retract" button for the machining center as represented by a machine control unit indicated at 28. The retract signal causes retraction of the machining center spindle. The drilling process may be resumed or continued at any time. A flow diagram of this operation is illustrated in FIG. 2.

In the specific embodiment under consideration, an additional monostable multivibrator (one-shot) 29 is connected to the output of the microcomputer 20 as shown. This one-shot can be implemented in software. The one-shot 24 between the comparator 18 and microcomputer 20 can also be implemented in software; this one-shot is used as a pulse stretcher and is used when the microcomputer is programmed on "status" rather than "interrupt". Software implementation of the one-shots is desirable to enable the system to be used to predict failure of small drills, as well as the wear of large drills, because of the wide variation in drill rpm. It is advantageous to use a software one-shot for the one-shot 24 between the comparator 18 and microcomputer 20, if wear of a large number of drills is to be measured, because of the greater ease in which a software one-shot pulse duration may be changed.

As discussed above, a calibration routine in the operating program for the microprocessor is used to permit the system to automatically adapt to the signal level from the accelerometer based on the level present when the operator determines that the drilling operation is "normal". This routine, and the overall operational program of the microprocessor, are quite straight-forward as can be appreciated from the description above and the drawings and the description which follows, and the programming necessary would be well within the ken of those of ordinary skill in the art.

Calibration is initiated by closing a momentary switch 33 which causes an interrupt.

Figure 3:
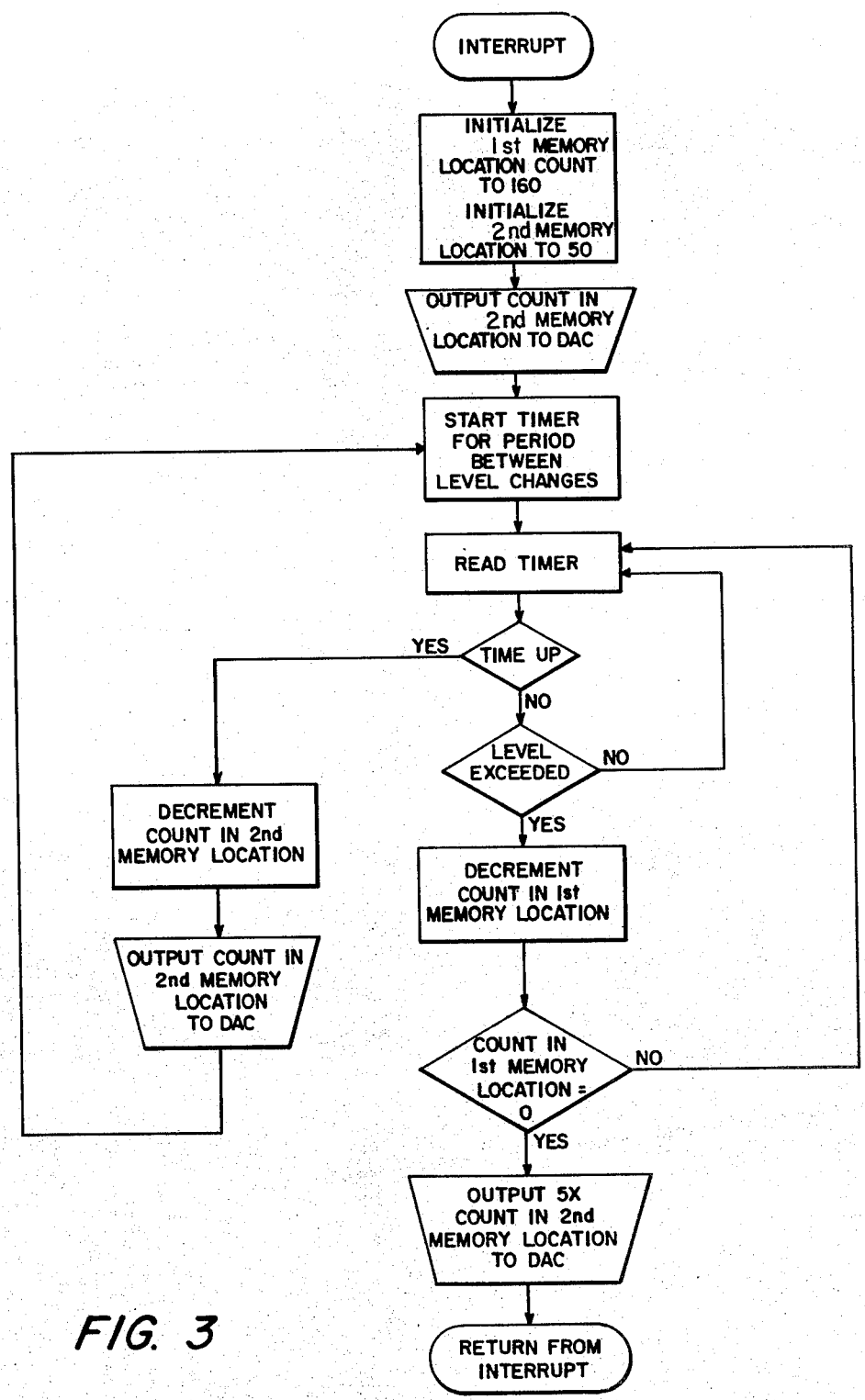
FIG. 3 is a flow chart of diagram of the calibration procedure.

Turning to the calibration routine itself, the "normal" operation referred to occurs when, for example, the cutting edge is sharp and symmetrical, there are no local hard areas in the workpiece due to cold working during manufacture, and the lubrication provided is adequate. The routine reduces the threshold level applied to the analog comparator 18 from approximately one-fifth of full scale (10 volts in a specific example) in increments and at fixed time intervals. In the specific embodiment under consideration, the steps are 0.04 volts at 1.5-second intervals. This incrementing operation continues until the peaks of the signal produced by the accelerometer begin to exceed the threshold. This is determined by the microcomputer 20 by counting the pulses that appear at the input terminal. In a specific example, when 160 pulses are detected, the level for a normal drilling operation has been found. The microcomputer 20 then applies an output signal to the D/A converter 22 which sets the threshold level to five times the normal drilling level. This operation is illustrated in the flow diagram shown in FIG. 3. It should be appreciated that there are other methods for determining the correct threshold other than reducing the threshold in fixed steps; for example, successive approximating techniques can be used.

A digital voltmeter 30 is used to display the threshold value in volts. An indicator light (not shown) is activated to indicate that a calibration operation is in progress. The system is put into operation to detect potential drill breakage immediately upon termination of the calibration operation. A nominal threshold level, e.g., 2.4 volts, is set when the power is initially applied.

In an advantageous embodiment, test points are provided to monitor the amplified accelerometer signal (the output of the amplifier 16), the threshold level (the output of the D/A converter 22), the pulse input to the microcomputer 20 (the output of the one-shot 24), and the retract signal that activates the retract relay 26. A red indicator light (not shown) indicates that a retract operation has been initiated. A switch 32 is used to enable or disable the retract signal applied to the machine control unit 28. When the switch 32 is in the disable position, so at to effectively override the retract signal, the system continues to operate and the red indicator light, referred to above, indicates that a retract operation would have occurred.

Considering a specific example, the system incorporating the invention was tested by drilling 0.043-inch diameter holes in a ¼-inch thick mild steel (1020) cold rolled plate, corresponding to workpiece 12. An accelerometer, corresponding to that indicated at 10 and having a sensitivity of 90 mV/G and an unmounted resonance of 18.2 kHz, was magnetically mounted to the plate. The drill (14) was lubricated by flood cooling with a water-soluble cutting-oil fluid and water mix. In order to induce drill failure, the lubrication was turned off. In 47 out of 50 cases the system retracted the drill before failure occurred. In each case, after the drill had been retracted, the retract signal to the machining center or control (28) was disabled and drilling was resumed. Depending upon the location of the drill on the plate, without lubrication the drill failed after drilling 2 to 5 holes at one location and 10 to 20 holes at another location. This variation was due to cold working of the plate when the plate was manufactured, resulting in local hard spots. In two cases the machining center (28) could not remove the drill in time, even though the retract signal had activated the retract relay (26) and the spindle retracted.

In one case, the lubrication was not turned off. This particular drill was able to drill more than 1200 holes without failing. In drilling these 1200 holes, there were four system-induced retractions, the system determining that the dril was about to fail in these instances. It is not possible to determine how many of these times the drill would have actually broken or otherwise failed if not retracted.

The system of the invention also senses improper drilling or operating conditions that can lead to drill failure. For example, chip build-up underneath the cutting edge can cause drill failure if the chips are not removed by additional lubrication and removal of the drill. To show this, lubrication of the drill was stopped until the system commanded the machining center to retract the drill. Then, without changing the drill, lubrication was started and holes were drilled.

With a new drill and proper lubrication there will be no output from one-shot 24. When drilling proceeds a situation may develop where the threshold of comparator 18 is exceeded and a number of sequential pulses less than four is produced by one-shot 24; under these circumstances, the drill is not retracted. The production of such pulses can be caused, for example, by chip build-up, i.e., by a chip getting caught in the drill flute. This is very common in drilling and is not an appropriate reason for retracting the drill. It is noted that a system based on amplitude detection would cause retraction of the drill under these circumstances, and this would be classified as a false alarm. It will be recognized that false alarms are almost as detrimental as broken tools because of the unnecessary machine down time associated with unneeded changing of a tool. However, with the present invention, if four pulses are produced in sequence, the system causes retraction of the drill. Under the circumstances, the criteria for improper drilling and imminent drill failure have been met. On the other hand, as noted, if any of the four pulses were missing, the criteria would not be met and the drill would not be retracted.

It is pointed out that the system of the invention uses a microcomputer because it is easy to implement random logic in a microcomputer and branching is simpler in a microprocessor. However, it should be understood that the system of the inventor could be implemented using random logic.

Although the invention has been described relative to an exemplary embodiment thereof, it will be understood that variations and modifactions can be effected in this exemplary embodiment without departing from the scope and spirit of the invention.

We claim:

1. A system for monitoring the operation of a rotating machine tool or part and for producing an output indicating that failure of that rotating tool or part is imminent or excessive wear of that rotating tool or part is present, said system comprising:

transducer means for producing an electrical output signal responsive to the mechanical vibrations by the tool or part being monitored;

comparator means for comparing said output signal with a variable threshold signal related to normal operation of the tool or part being monitored and for producing an output when the output signal of said transducer means exceeds said threshold signal; and monitoring and calibrating means for, during a monitoring mode of operation of said system, monitoring said comparator means to detect when a said output is produced by said comparator means and producing a control signal indicating that failure of the tool or part is imminent or that excessive wear of the rotating tool or part is present, when, upon initially detecting a said output, a further said output is also detected thereby during each of a predetermined number of successive time intervals related to the rotational speed of said tool or part and for, during a calibration mode of operation of said system, monitoring the output produced by said transducer means during the normal operation of the tool or part to establish a said variable threshold signal.

2. A system as claimed in claim 1 wherein said transducer means comprises an accelerometer.

3. A system as claimed in claim 1 wherein said transducer means comprises a piezoelectric accelerometer mechanically coupled to a workpiece associated with the tool or part.

4. A system as claimed in claim 1 further comprising an amplifier having a high input impedance connected to the output of said transducer means.

5. A system as claimed in claim 1 wherein said tool or part is a drill, and said number of successive intervals is four.

6. A system as claimed in claim 1 wherein said monitoring and calibrating means comprises microcomputer means.

7. A system as claimed in claim 6 wherein said microcomputer means, during said calibration mode of operation, reduces the threshold level from a predetermined fraction of the full scale voltage value by predetermined increments for predetermined intervals until a level is reached wherein a selected number of said pulses are sampled by said microcomputer means, said microcomputer means then generating, as said threshold signal, a signal which is a predetermined multiple of the level reached.

8. A system as claimed in claim 1 wherein output pulse producing means are connected to said comparator means for producing an output pulse when the output signal of said transducer means exceeds said threshold signal and wherein said monitoring and calibrating means monitors the output pulses produced by said output pulse producing means.

9. A system as claimed in claim 8 wherein said pulse producing means comprises a monostable multivibrator.

10. A system as claimed in claim 8 or claim 9 wherein said pulse producing means produces a pulse whose duration is slightly less than the period of rotation divided by the number of cutting edges or segments of said tool or part and said monitoring and calibrating means, upon initially detecting a said pulse, samples the output of said pulse producing means at time intervals equal to the period of rotation of said tool or part.

* * * * *